United States Patent [19]

Banks et al.

[11] Patent Number: 4,476,734

[45] Date of Patent: Oct. 16, 1984

[54] WET NEEDLE SAMPLER FOR USE WITH A GAS CHROMATOGRAPH

[75] Inventors: Thomas M. Banks, Waterbury, Conn.; Raymond R. Ruckel, Garrison, N.Y.; Samuel F. Spencer, Danbury; John Q. Walker, Brookfield Center, both of Conn.

[73] Assignee: International Business Machines Corporation, Armonk, N.Y.

[21] Appl. No.: 472,900

[22] Filed: Mar. 7, 1983

[51] Int. Cl.$^3$ ............................................. G01N 1/14
[52] U.S. Cl. ............................. 73/864.16; 73/864.21; 73/864.22; 73/864.85
[58] Field of Search ............... 422/100; 73/864.12, 73/864.15, 864.16, 864.17, 864.21, 864.22, 864.85, 864.86, 864.87

[56] References Cited

U.S. PATENT DOCUMENTS

| | | | |
|---|---|---|---|
| 3,508,442 | 4/1970 | Lightner et al. | 73/864.87 |
| 3,529,475 | 9/1970 | Lightner et al. | 73/864.87 |
| 3,800,984 | 4/1974 | Phelan | 422/100 |
| 4,130,394 | 12/1978 | Negersmith | 422/100 |
| 4,429,583 | 2/1984 | Watanabe | 73/864.17 |

Primary Examiner—S. Clement Swisher
Attorney, Agent, or Firm—James E. Murray

[57] ABSTRACT

The flushing of the syringe with a side port is performed by introducing a liquid solvent through the side port while the plunger is retracted from the barrel. At the completion of the flushing operation the plunger is fully inserted into the barrel expelling all the solvent except that in the needle. The needle is then inserted into the sample and the plunger is raised to withdraw the sample. With this arrangement, it is possible to take a 0.1 L sample and dispense it because of the solvent reserve in the barrel. Furthermore, the solvent reserved in the barrel provides a buffer so that sampled material does not contact the plunger or get into the annular space around the retracted plunger.

6 Claims, 6 Drawing Figures

FIG. 3
FIG. 4
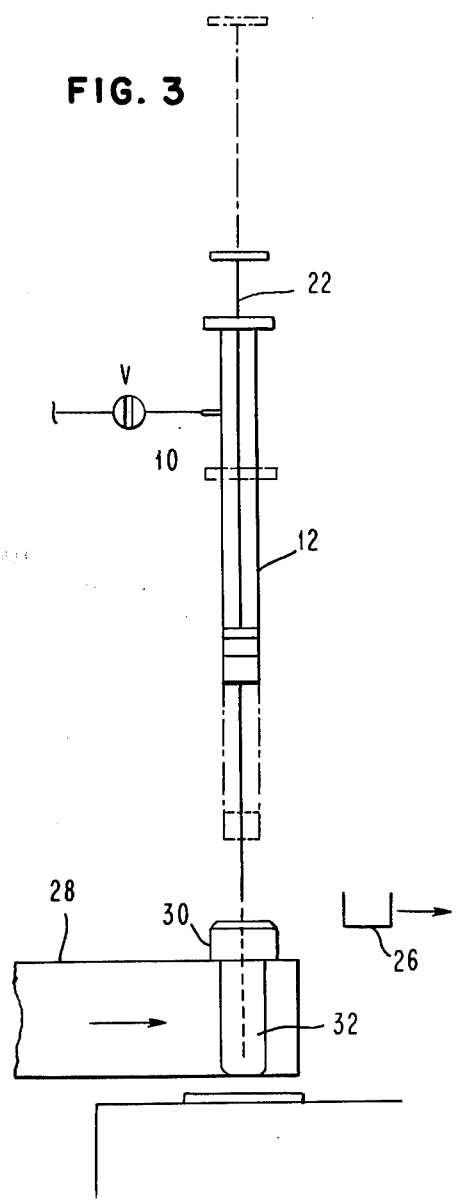
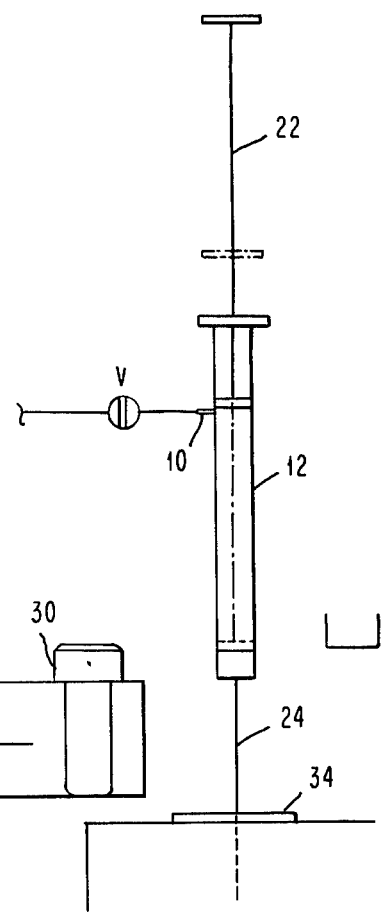

WET NEEDLE SAMPLER FOR USE WITH A GAS CHROMATOGRAPH

The present invention relates to the taking of samples for analysis by a gas chromatograph and more particularly to a method and apparatus for sequencing the operations of a syringe for taking such samples.

Two known types of samplers involve the use of a syringe in which a plunger moves in a passage of a barrel to eject the liquid samples out through a needle into the injection port of a gas chromatograph.

In the first type of sampler, the plunger is used to draw a sample into the syringe through the needle and then force that sample out through the needle into an injection port of the chromatograph. After the sample has been dispensed into the injection port, the needle is flushed. Flushing is accomplished using the plunger to draw a solvent up into the syringe through the needle and then ejecting it through the needle. Contamination is a problem with this arrangement. It is difficult to prevent air from being trapped in the syringe and to guarantee a proper cleaning of the syringe. To obtain an airless sample and to properly flush the syringe, it is necessary to use repeated cycles of the plunger. If the sampling is automated, manual intervention is sometimes necessary to avoid the air contamination.

The second type of sampler, has a syringe with a side port near the top of the barrel. With this arrangement, the plunger is withdrawn to the top of the barrel and the sample is introduced into the barrel through this additional port. The plunger is used to force the liquid out of the barrel into the injection port of the gas chromatograph. The flushing of the syringe is accomplished in much the same way. Liquid is introduced into the side port and forced through the barrel under low pressure into a waste cup. While this scheme effectively eliminates the air bubble problem, sample contamination is still a problem because the samples come in direct contact with plunger and the small annular space between the plunger and the barrel wall above the side port. Furthermore, large sample volumes are needed when this method of loading the syringe is used because the samples must fill the syringe and the lines attaching the sample wall to the side port. For instance, if a 10$\mu$l (micro liter) syringe is used at least 10$\mu$l of the sample must be used. The problem is aggravated when as suggested the sample liquid is used as the flushing agent.

THE INVENTION

In accordance with the present invention the second type of syringe is used in conjunction with apparatus that permits the taking of small uncontaminated samples. The flushing of the syringe is still performed through the side port to forward flush the needle. The liquid used in the flushing is a solvent. At the completion of the flushing operation the plunger is fully inserted into the barrel expelling all the solvent except that in the needle. The needle is then inserted into a sample and the plunger is raised to withdraw the sample. With this arrangement, it is possible to take a 0.1$\mu$L sample and dispense it because of the solvent reserve in the barrel. Furthermore, the solvent reserve in the barrel provides a buffer so that sampled material does not contact the plunger or get into the annular space.

Therefore, it is an object of the present invention to provide a new method and/or apparatus for the taking and dispensing of samples in gas chromatography;

It is another object of the present invention to provide a new method and/or apparatus for taking and dispensing small samples in gas chromatography, and It is a further object of the present invention to provide a new apparatus and/or method for taking and dispensing uncontaminated samples in gas chromatography.

THE DRAWINGS

These and other objects of the present invention can best be understood by reference to the embodiment of the invention illustrated by the accompanying drawings of which:

FIGS. 1 to 4 are schematic representation of the operation of a sampling device in accordance with the present invention;

DETAILED DESCRIPTION

Figure 1:
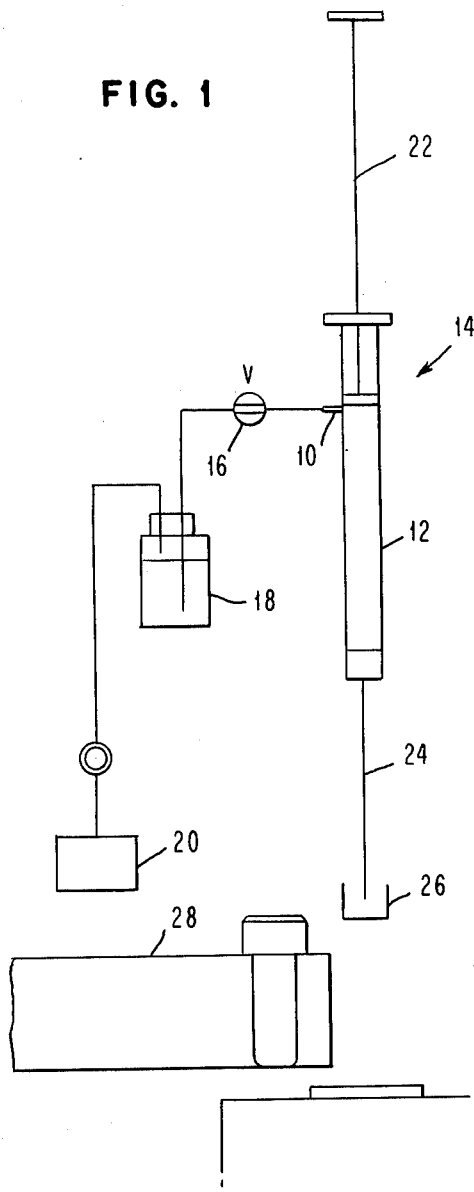

In FIG. 1, the side port 10 in the barrel 12 of the syringe 14 is connected through valve 16 to a solvent reservoir 18. A pressure source 20 is also connected to the solvent reservoir through a regulator 22. During the solvent flush of the syringe 12 the valve 16 is open to allow solvent from reservoir 18 to pass through port 10 into the barrel 12. With the plunger 22 withdrawn to above the port 10, liquid solvent under low pressure from source 20 will be flushed through the needle 24 of the syringe and into a waste cup 26.

Figure 2:
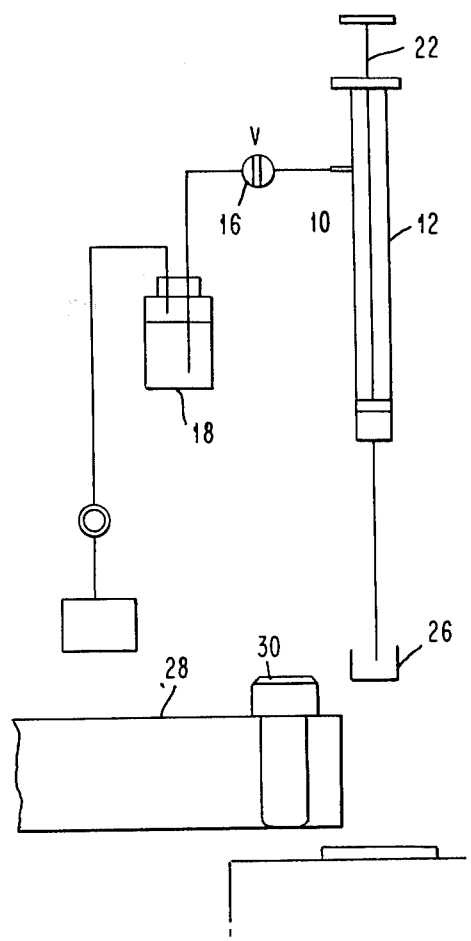

Flushing of the needle in the forward direction continues until the syringe is clean. Then as shown in FIG. 2 the valve 16 is closed and the plunger is fully inserted into the barrel 12, expelling all the solvent except for that remaining in the needle 24.

As shown in FIG. 3 the waste cup 26 is now moved away from under the syringe and a sample tray moved to bring a vial 30 under the needle 24. The syringe is then lowered so that the needle pierces the septum of the sample vial and enters the liquid sample 32. With the needle in the sample, the plunger is withdrawn until sufficient liquid is removed from the vial. This does not have to be much and may be less than needed to fill the needle 24. The liquid solvent backs up the sample in the barrel to facilitate ejecting of the small sample and to prevent contamination of later samples as explained previously.

In FIG. 4 the sample tray 28 has been withdrawn and the syringe is lowered so that the needle enters the inject port 34 of the gas chromatograph. The plunger is then thrust fully into the barrel to expel the sample. The solvent back-up assures that the whole sample is expelled. After the sample has been injected the syringe is returned to the solvent flush position with the plunger extracted and the waste cup positioned under the needle.

Figure 5:
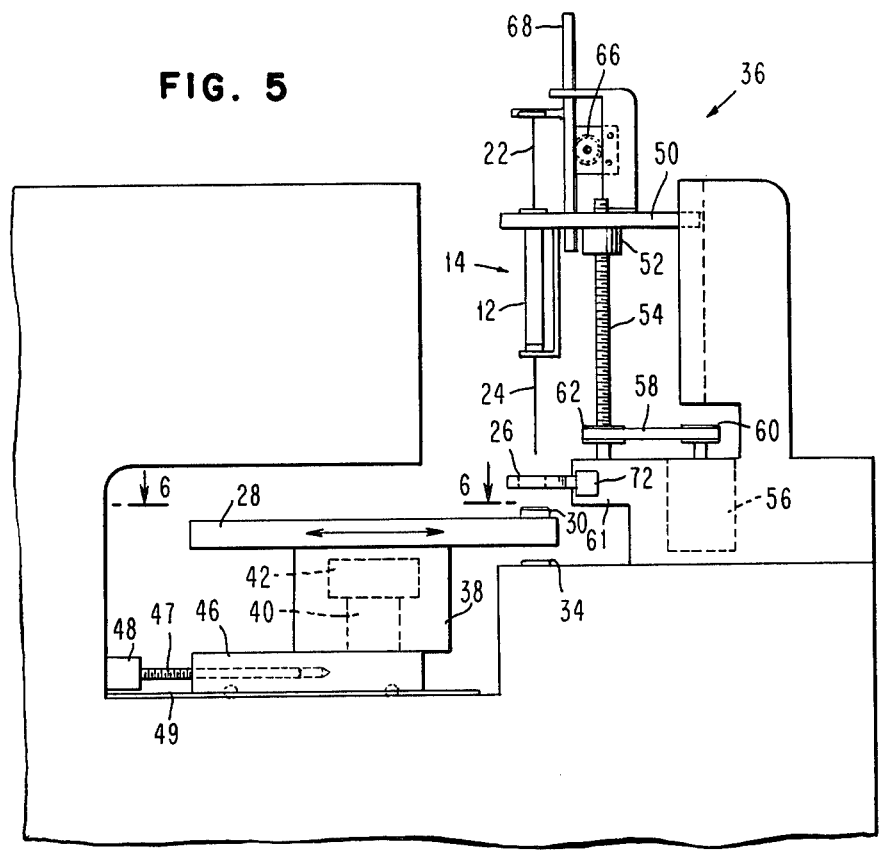
FIG. 5 is a plan view of sampling apparatus incorporating the present invention.
Figure 6:
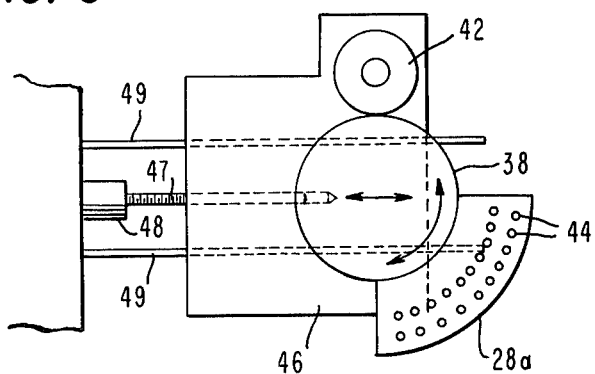
FIG. 6 is a plan view taken along line 6—6 in FIG. 5 with three of the four tray segments sensored to expose the undercarriage for the tray assembly.

Referring to FIGS. 5 and 6 the sampling head 36 is mounted on the gas chromatograph with the needle 24 poised over the inject port 34. The sample tray assembly is placed facing the sampling head 36 so that the tray 28 can be moved in and out of postion under the syringe. The tray 28 is actually a four segment carousel in which each segment is mounted on a central drive hub 38 driven by a stepping motor 40 through a frictional rubber wheel 42 to rotate the trays for positioning the different receptacles 44 in the tray containing the sample vials under the needle. The hub and the tray are rotatably mounted on a carriage 46 and the motor 40 is fixed to that carriage. The carriage is driven through a lead screw 47 by a stepping motor 48 along guide rails 49 to position the receptacles 44 into and out of the sampling position. With motors 40 and 48, any one of the receptacles 44 can be positioned under the needle and the tray 28 can also be moved away from the needle 24 so that does not interfere with the flushing of the syringe 14 and the injection of samples into the gas chromatograph.

The barrel 12 of the syringe 24 is mounted in a carriage 50 containing a nut 52 mounted on a lead screw 54 driven by a stepping motor 56 through a belt 58 and pulleys 60 and 62. This permits movement of the barrel 12 vertically relative to the frame 62 of the sampling head 36.

The drive for the plunger 22 is carried by the carriage 50. A stepping motor 66 is fixed to a bracket 68 that sits on the carriage 50. The stepping motor 66 drives a rack 68 which is attached to the plunger 22 and moves freely with respect to the carriage 50 so that the plunger 22 can be moved independently of the barrel 12. The waste cup 26 is pivoted on the frame 62 so when it is not is use it can be rotated out of the way by a solenoid actuated arm 72.

Above we have described one embodiment of our invention. It should be understood that many modifications and changes can be made in the illustrated embodiment without departing from the spirit and scope of the invention as represented in the attached claims.

Having thus described our invention, what we claim as new and desire to secure by Letters Patent is:

1. In an automatic sample handler having a syringe with a barrel with a needle at one end and a plunger inserted into the barrel at the other end and also having a port through the body of the barrel, the method of taking samples comprising:
   (a) pumping a solvent into the port through the barrel and out the needle while the end of the plunger is withdrawn beyond the port so that the syringe is back flushed of contaminants and the barrel filled with solvent,
   (b) inserting the end of the plunger past the port in the barrel to expel through the needle solvent introduced by step (a), and
   (c) drawing a liquid sample material up into the barrel through a needle by partially withdrawing the plunger from the barrel after completion of cleaning of the syringe using steps (a) and (b) to take a sample.

2. The method of claim 1 including the additional step (d) of expelling the sample from the syringe into a gas chromatograph through the needle by inserting the plunger into the barrel.

3. The method of claim 2 including inserting the plunger completely into the barrel during steps (b) and (d).

4. The method of claim 3 wherein in withdrawing the plunger in step (c) the plunger's movement is sufficient only to draw liquid into the needle and not into the barrel.

5. In an automatic sample handler having a syringe with a barrel having a needle attached to one end and a plunger inserted into the other end and also having a port through the body of the barrel, apparatus for taking samples comprising:
   (a) pumping means for forcing solvent through the port into the barrel and out the needle to flush the syringe of contaminants,
   (b) sampling means for relative positioning of the needle and liquid sample vials for introduction of samples in the vials into syringe through the tip of the needle, and
   (c) syringe actuation means both for movement of the plunger to withdraw the plunger during flushing of the syringe and the taking of samples and for movement of the barrel during insertion of the needle into sample vials.

6. The automatic sample handler of claim 5 including waste means for receiving liquid pumped through the syringe during flushing operations.

* * * * *